United States Patent [19]
Feldman et al.

[11] Patent Number: 5,943,719
[45] Date of Patent: Aug. 31, 1999

[54] METHOD AND DEVICE FOR PRECISE INVASIVE PROCEDURES

[75] Inventors: Andre Feldman, Haifa; Rafael Blumenthal, Kiriat Tivon; Ludmila Natanzon, Haifa, all of Israel

[73] Assignee: Picker Medical Systems, Ltd., Haifa, Israel

[21] Appl. No.: 08/960,204

[22] Filed: Oct. 29, 1997

[30] Foreign Application Priority Data

Nov. 1, 1996 [IL] Israel ................................. 119545

[51] Int. Cl.⁶ .................................................. A61B 19/00
[52] U.S. Cl. ....................................................... 6/130
[58] Field of Search ................................... 606/130, 129, 606/1; 350/321; 604/116

[56] References Cited

U.S. PATENT DOCUMENTS

| | | | |
|---|---|---|---|
| 4,580,560 | 4/1986 | Williamson | 606/130 |
| 4,651,732 | 3/1987 | Frederick | 128/303 R |
| 4,936,655 | 6/1990 | Leib et al. | 350/321 |
| 5,142,930 | 9/1992 | Allen et al. | 74/469 |
| 5,678,549 | 10/1997 | Heywang-Koebrunner | 606/130 |

*Primary Examiner*—Michael Buiz
*Assistant Examiner*—Vy Q. Bui
*Attorney, Agent, or Firm*—Fenster & Co., Patent Attorneys, Ltd.

[57] ABSTRACT

A method for inserting an invasive tool, including: attaching a frame to a human body adjacent to a portion of the body; acquiring an image of the body; determining a trajectory of the tool on the image; calculating points of intersection between the trajectory and two sheet which are adapted to be inserted into the frame; perforating the sheets at the calculated points; placing the sheet within the frame; and inserting the invasive tool through the perforations.

28 Claims, 8 Drawing Sheets

METHOD AND DEVICE FOR PRECISE INVASIVE PROCEDURES

FIELD OF THE INVENTION

The present invention relates generally to the field of invasive medical procedures, and specifically to accurate monitoring of invasive procedures with an imaging system.

BACKGROUND OF THE INVENTION

In minimally invasive medical procedures a needle, laser or other surgical tool is inserted into a patient's body. Minimally invasive procedures are performed for several reasons, such as taking tissue samplings, abscess drainage, laser ablation, screw insertion, teeth implantation etc. One common minimally invasive procedure is the biopsy procedure which involves guiding a needle along an anatomical trajectory to an anatomical location in the patient's body. For example, a biopsy needle may be used to take a sample from a lesion in the patient's body. These minimally invasive procedures are becoming more common because they serve as alternatives to full scale surgery.

Nevertheless, biopsy procedures are painful medical procedures. In addition, inaccurate movements could cause severe damage to healthy organs of the patient, for example, puncturing a main blood vessel.

In order to accurately perform the biopsy procedure, a biopsy needle trajectory is commonly planned before insertion of the needle. The planning is usually performed on images acquired by imaging systems such as computed tomography (CT), ultrasonography and magnetic resonance imaging (MRI). The needle trajectory is chosen so as to minimize unnecessary damage to tissue in the patient's body.

But although exact planning is feasible, implementing the planned trajectory is not simple. Ordinarily, the surgeon sees only the patient's skin. In some cases internal landmarks such as the bone structure of the patient can help orient the surgeon, but in most cases, especially in abdominal biopsies, such landmarks do not exist. Furthermore, the patient's body can move and the orientation of his inner organs can change, between the acquisition of the image and the invasive procedure. In longer procedures or if there is a considerably delay between image acquisition and the biopsy procedure, there is a high probability that the trajectory as planned (on the image) will not match the anatomical trajectory (as performed).

As a result, in many biopsy procedures, multiple trials of needle insertion are necessary to position the needle at a desired anatomical location within the patient.

Several solutions to precise biopsy needle guiding have been developed. One solution is a use of rigid guides, along which a biopsy needle is guided into the body. These rigid guides provide precise positioning of the biopsy needle but usually have a limited range of angles at which a needle can be inserted. In some head procedures a stereotactic frame is used to guide a needle into the patient's head. This frame is cumbersome, blocks the view of the surgeon and may also interfere with the surgeon's movements. Stereotactic frames are also used for spinal procedures.

Another solution uses tracking devices. In this method either a relatively large brace-like structure or three fiducial implants are temporarily attached to the patient's body, before imaging. In the resulting image, the fiduciary marks or the frame are used to generate an external reference frame, to which the planned needle trajectory is registered. Such a system is described for example in U.S. Pat. No. 5,142,930, whose disclosure is incorporated herein by reference. The '930 patent describes a system comprising an articulated arm, in which positional encoders are used to determine the location of a tool mounted on the arm. Various invasive tools may be attached to the arm. The position of the distal tip of the invasive tool is continuously calculated and transmitted to a computer. The computer controls an imaging apparatus to acquire images, including a slice which contains the tip of the invasive tool. In this method the images are real-time images. In another known method the computer displays previously acquired images based on the tool position.

U.S. Pat. No. 4,651,732, whose disclosure is incorporated herein by reference describes another method in which a light beam marks the trajectory chosen for a biopsy needle. While performing the biopsy the surgeon guides the needle into the patient's body by following the light beam.

SUMMARY OF THE INVENTION

It is an object of the present invention to provide apparatus to assist a surgeon in accurately performing minimally invasive procedures such as biopsy procedures, screw insertion, abscess drainage and tooth implantation.

It is an object of some embodiments of the present invention to provide a compact device which can provide high accuracy in minimally invasive procedures.

It is a further object of some embodiments of the present invention to provide a simple method for highly accurate minimally invasive procedures.

It is another object of some embodiments of the present invention to provide apparatus which will keep an invasive tool in place during an intermission in the invasive procedure. The apparatus also allows for scanning of a patient during the intermission without unduly irradiating the surgeon.

In accordance with the present invention, a trajectory of an invasive tool such as a biopsy needle is defined by holes in two or more sheets situated outside the patient, wherein the sheets are preferably generally parallel to the skin of the patient. The holes define a straight line along which the biopsy needle is guided into the patient.

In accordance with one embodiment of the present invention, at least two rigid frames are fixedly related to each other, and are fixed on a patient. Within or on each of the frames a, preferably hard, sheet is placed with high precision. On each of the sheets a point is marked and pierced, the points defining together a straight line. The straight line serves as the trajectory of the biopsy needle.

After the frames are firmly placed so that they can be used as an accurate reference frame, images of a region in the patient's body, which includes at least part of the trajectory, are acquired using an imaging system. Preferably, at least three markers, comprised of a material easily imaged with a high contrast by the imaging system, are embedded within the frame, preferably within legs of the frame. As an example, for CT imaging such a material could be lead or aluminum. These markers serve as reference points on the images and are also preferably visually identifiable on the frames.

After image acquisition, a three dimensional reconstruction of the scanned volume is preferably performed, as known in the art. The surgeon chooses the best trajectory for inserting the biopsy needle to the desired spot in the patient's body, usually based on the anatomical information provided by the images. The surgeon inputs the chosen trajectory into the computer, preferably, by marking the trajectory on one of the images. For example, by defining two points, i.e., the entry and destination points. In one preferred embodiment of the invention, the surgeon inputs the location of the frames into the computer. Preferably, the surgeon marks the locations of at least three of the markers on at least one of the images. Alternatively, the computer automatically locates the markers based on their shape and/or the material of which they are composed.

Given the trajectory, the computer calculates the coordinates corresponding to intersection points between the chosen trajectory and the sheets. Holes corresponding to the intersection points may be automatically drilled into the sheets or, alternatively, marks may be printed on the sheets by a printer, after which the sheets may be perforated at the intersection points by machine or manually. Markings which guide the sheets precisely into their place within the frames may also be printed on the sheets.

Thereafter, the sheets are washed and/or sterilized, if necessary. The biopsy needle is guided and inserted into the patient's body through the holes. The holes define the trajectory of the needle and in particular the entrance point and the entrance angle. Because the entrance angle is determined by the relative location of the holes, the accuracy in determining the angle is proportional to the distance between the sheets. Therefore, to increase the accuracy in determining the entrance angle, the sheets are preferably fixed at a distance from each other of at least the order of the distance from the surface of the patient to the lesion.

Preferably, the holes have a form of a truncated cone, such that a narrow end of the hole has a cross-section similar to a diameter of a biopsy needle. Alternatively, the hole axis is formed parallel to the planned trajectory. Alternatively or additionally, a slightly elastic material, such as hard rubber, is used for the sheet, or as a border for the hole.

In some embodiments of the present invention the sheets are not perforated in real-time. Rather, pre-perforated sheets are used and existing holes are chosen, one from each sheet, to define the trajectory.

In a preferred embodiment of the present invention, two movable planes are used. Each plane is pierced by at least one hole and preferably by an array of prepared holes. The holes preferably have a truncated cone shape, to allow the biopsy needle to achieve large angles with the planes. The planes can be moved, independently of each other, in both x and y directions, while being maintained an a parallel configuration. Precise alignment of the planes is preferably achieved using micrometers.

The computer selects two holes, one from each plane, based on the planned trajectory and reports to the surgeon which holes were chosen. The computer also determines the precise position of the planes so that the two selected holes are aligned with the chosen trajectory. Movement of the planes can be performed either by the surgeon or automatically by computer controlled micrometers or motors. Once the planes are in place, the planes are preferably secured by screws, clamps or by another method so that they do not move during the biopsy procedure.

It is noted that although two planes are sufficient to definitely form a trajectory, more than two planes may be used to increase accuracy and/or robustness of the needle guidance.

In further embodiments of the present invention the trajectory is defined by a guide located within the holes. The guide allows easy introduction of a biopsy needle into the patient and supports the needle during the biopsy process. This allows the surgeon to leave the area during the operation of the imaging system, which system may emit harmful radiation. The guide may be inserted into the holes after they are properly located, or alternatively, the guide is permanently located in the holes and moves with the planes.

The above mentioned frames and planes are, preferably, rigidly constructed so that they do not change their position and orientation during a biopsy procedure. However, preferably, they allow for slight changes to be made by the surgeon after the invasive procedure has begun. The necessity for such changes may be made apparent to the surgeon by any of the known verification methods, such as those described below.

One such verification method involves using a tracking device. The biopsy needle is attached to a tracking device, that can determine at any moment the position and orientation of the biopsy needle relative to a reference location on the patient. Tracking devices include, a mechanical attachment with motion encoders, an ultrasound tracking system, a video tracking system, a magnetic field tracking system and other tracking systems, as well known in the art. A three dimensional internal coordinate system is defined, preferably, using the markers embedded within the frames, although any three non-collinear points may be used. Either the surgeon marks the three points on one of the images, or the computer automatically locates the markers, preferably, according to their shape and color on the images and/or their computed density.

Before the invasive procedure begins, the biopsy needle tip is brought into proximity with an initialization point in the relevant region of the patient's body. The computer tracks the location of the needle tip in the internal coordinate system and performs any necessary translations between the internal coordinate system and an existing external coordinate system. Thus, any deviation of the needle tip from the planned trajectory is easily detected.

Preferably, images of anatomical slices which include the tip of the biopsy needle are displayed by the computer based on the calculated position of the needle tip. These images may be pre-stored images. Alternatively, new images are interpolated from previously stored images responsive to the insertion angle of the needle.

Using coordinates received from the tracking system, the computer changes the display so that the display is always of a slice containing the plane of the biopsy needle. Preferably, the position of the needle tip is marked on every displayed image. As the surgeon moves the needle, the displayed image is updated in real time. The display is updated at a suitable rate, such as about three images a second, so that the surgeon can easily guide the needle along the chosen trajectory.

In addition, in some embodiments of the present invention, new images may be acquired during the biopsy procedure. Oblique images may be interpolated from axial images, for example as described in U.S. Pat. No. 4,674,046, to Ozeki et al., the disclosure of which is incorporated herein by reference.

Preferably, a scan of the plane containing the chosen trajectory is performed by the imaging system after the sheets are positioned, and before the biopsy needle is inserted into the patient. In addition, after inserting the needle, the surgeon may direct the imaging system to perform verification scans, to check if the chosen trajectory is being accurately followed and if the patient or any of his organs have moved since the previous scan. Both the old image and the new image may be displayed side-by-side. The new images may be used for a real-time image display, as described above. If necessary, a new trajectory is chosen for the biopsy needle. A new trajectory may require new sheets to be prepared or that the location of existing sheets be modified. Such verification scans are performed especially before important steps in the procedure, such as taking tissue samples.

In order to minimize the influence of the patient's respiration, which may cause internal motion of target organs, a respiratory belt can be used to gate the procedure. Preferably, the respiratory belt automatically gates all steps of the invasive procedure, including the preliminary scanning, causing them to be carried out at the same phase of respiration. Alternatively, or in addition, the respiratory belt signals the surgeon, for example, during time periods when actions such as movement of the needle may be carried out.

It is also noted, that although the invention has been described in conjunction with a biopsy needle, it can also be used in many other minimally invasive procedure such as tooth implantation, inserting screws, abscess drainage etc.

The present invention will be more fully understood from the following detailed description of the preferred embodiments thereof, taken together with the drawings, in which:

DETAILED DESCRIPTION OF PREFERRED EMBODIMENTS

Figure 1:
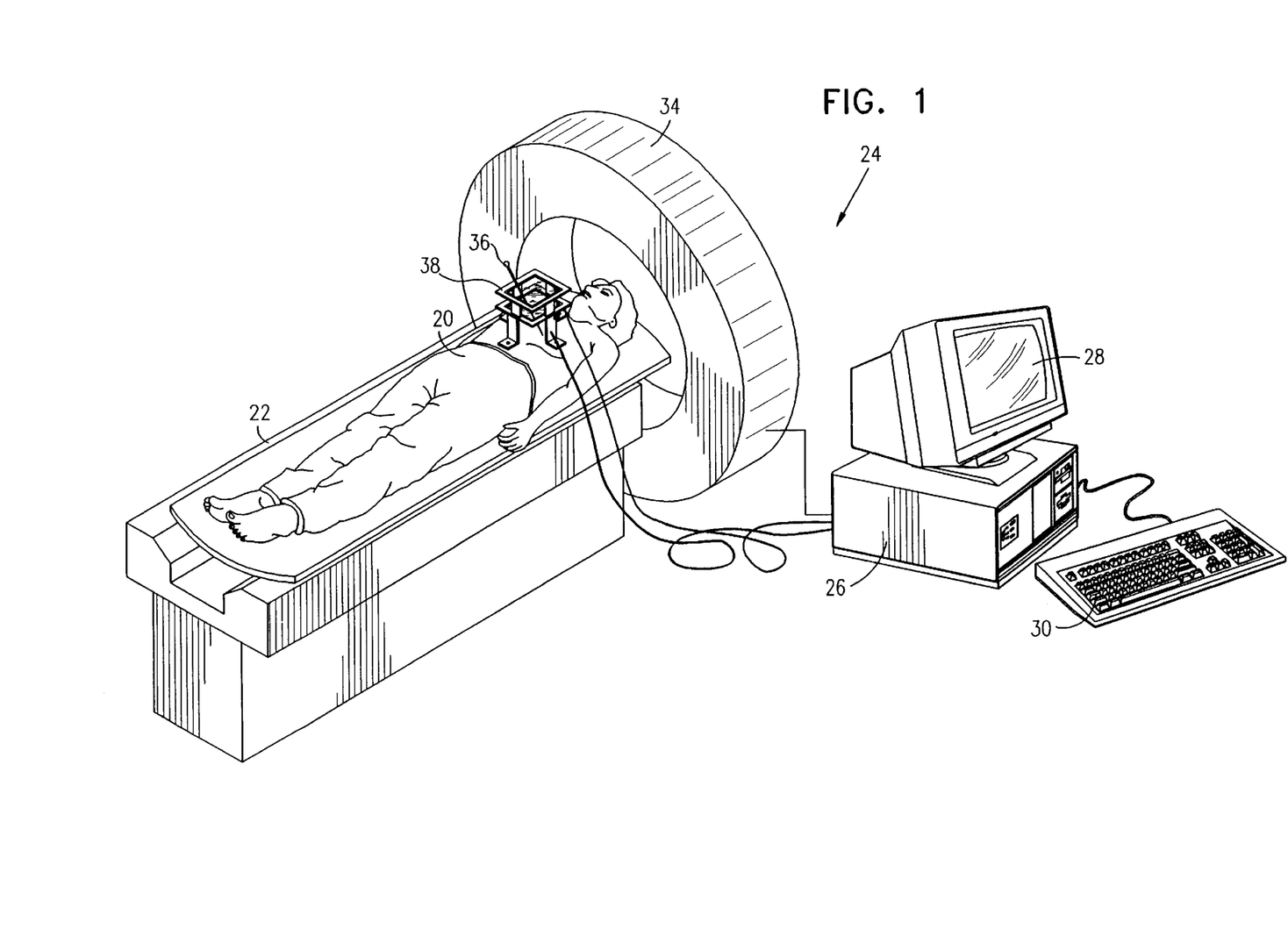
FIG. 1 is a perspective view of a patient ready for an invasive procedure according to a preferred embodiment of the present invention.

Reference is now made to FIG. 1, which shows a computed tomography (CT) imaging system 24, operative in accordance with a preferred embodiment of the present invention. Imaging system 24 comprises a bed 22 on which a patient 20 lies while his body is imaged. Imaging system 24 further comprises a gantry 34 containing X-ray generators and detectors and preferably a processor which performs calculations for reconstruction and reformation of images. A programmable computer 26 may control the imaging system, and the other apparatus described below. Computer 26 has a screen 28 which displays one or more reconstructed and/or reformatted images and an input unit 30 which receives commands from a surgeon using the present invention.

Figure 2:
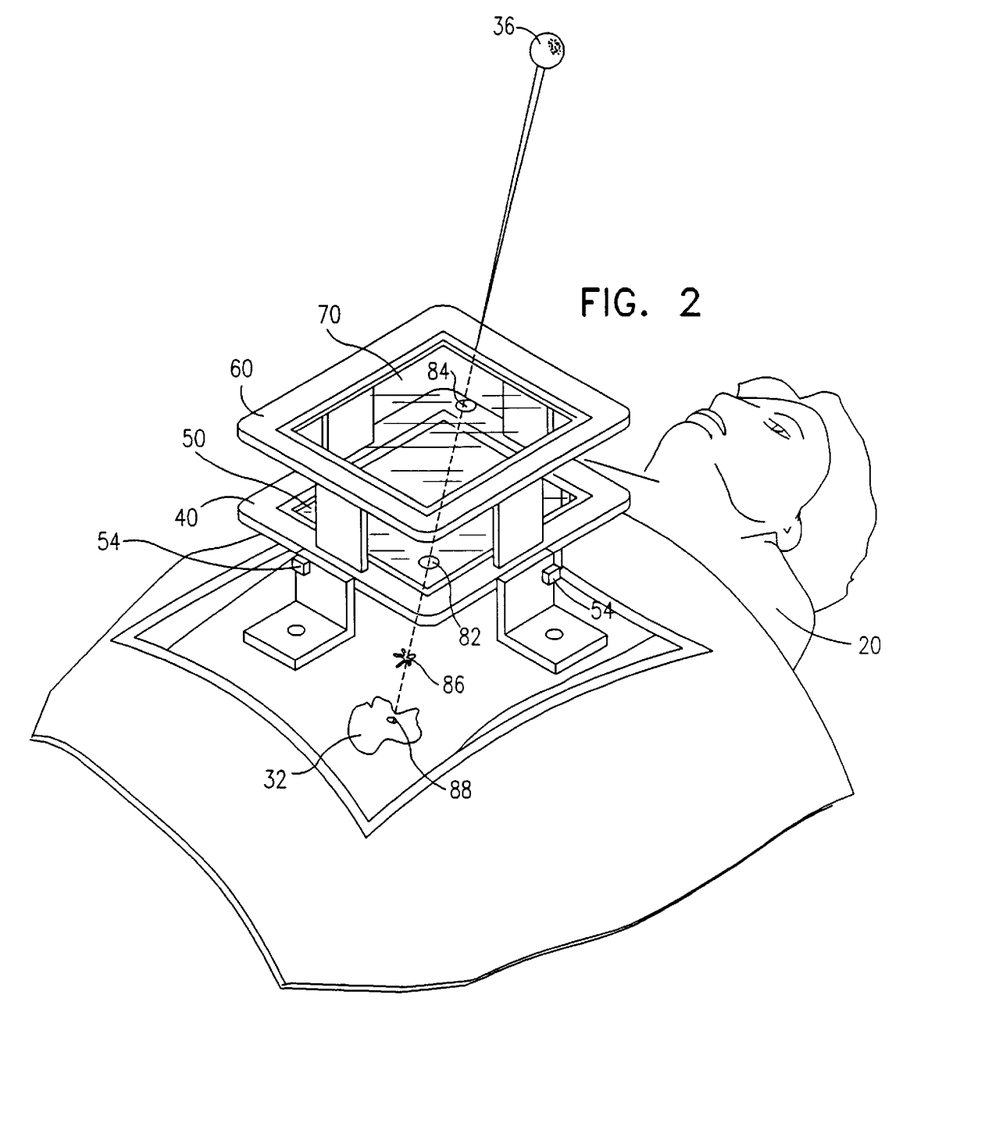
FIG. 2 is a perspective view of a frame set in accordance with a preferred embodiment of the invention and a chosen trajectory for a biopsy needle.

Reference is now made to FIG. 2 which shows a trajectory 80 along which a needle 36 is to be guided into the patient, in accordance with a preferred embodiment of the present invention. A sample is to be taken from a lesion 32 within patient 20 for laboratory testing. Fastened to the patient's skin, above lesion 32, is a frame-set 38. Fastening may be accomplished using a belt, surgical screws, a clamp, adhesive or any other method of fastening known in the art which will keep frame-set 38 precisely in place with respect to patient 20. The method of fastening is chosen according to the part of the body to which frame-set 38 is to be fastened. Accordingly, when connecting frame-set 38 to a rigid part of the body, such as the skull, screws are ordinarily used. On the other hand, when fastening to soft parts of the body, such as the stomach, either adhesive or a belt or both of them are preferably used.

Frame-set 38 preferably comprises at least two separate frames, a lower frame 40, and an upper frame 60. Lower frame 40 is adapted to precisely receive a lower sheet 50, and frame 60 is adapted to precisely receive an upper sheet 70. Within frame-set 38 there are, preferably, at least three fiducial markers 54 embedded in at least three non-collinear points. Markers 54 preferably comprise a material easily identified on images produced by imaging system 24.

After frame-set 38 is fastened to patient 20, the CT imaging system preferably performs a scan of a region containing lesion 32. The results of the scan are used to reconstruct slice images covering the scanned region. Using control unit 30 the surgeon can display any of the images on screen 28. Examining the images, the surgeon chooses a trajectory 80 best suited for guiding biopsy needle 36 to lesion 32. Trajectory 80 is usually chosen to cause minimal damage to tissue and organs of patient 20 and/or to maximize the probability of success of the procedure. The surgeon indicates the chosen trajectory to computer 26, preferably, by marking on an image, an entrance point 86 into the patient and a destination point 88 within lesion 32. Computer 26 translates trajectory 80 to all the reconstructed images. The surgeon also, preferably, indicates on one of the images at least three points, preferably markers 54, which serve as reference points for computer 26. The design of frame-set 38 is preferably permanently stored in computer 26, so computer 26 knows the location of every point on frame set 38 and on sheets 50 and 70 with respect to markers 54.

Knowing entrance point 86 and destination point 88, computer 26 calculates the coordinates of a straight line connecting points 86 and 88, which is collinear with trajectory 80. Computer 26 further calculates the coordinates of intersection points between chosen trajectory 80 and sheets 50 and 70.

Markings which designate the intersection points are printed on sheets 50 and 70. Sheets 50 and 70 are perforated by the surgeon at the markings, to form holes 82 and 84. After perforation, sheets 50 and 70 are sterilized and the sheets are placed into their corresponding frames. Holes 82 and 84 preferably have a truncated cone shape, wherein hole 82 widens toward patient 20 and hole 84 widens away from patient 20. The narrow end of holes 82 and 84 preferably has a cross-section similar to the diameter of biopsy needle 36. This arrangement allows biopsy needle 36 to achieve large angles with respect to sheets 50 and 70 without the drilling of angled holes.

Biopsy needle 36 is inserted through holes 82 and 84 to follow trajectory 80 into patient 20. During the biopsy procedure, correspondence between the actual and planned anatomical trajectories is preferably verified. The verification may be done using any of the methods known in the art and especially use those methods which will be described below. If deviation from trajectory 80 is discovered, the procedure may be reinitiated. Alternatively, slight adjustments may be performed in a manner described below.

Figure 3:
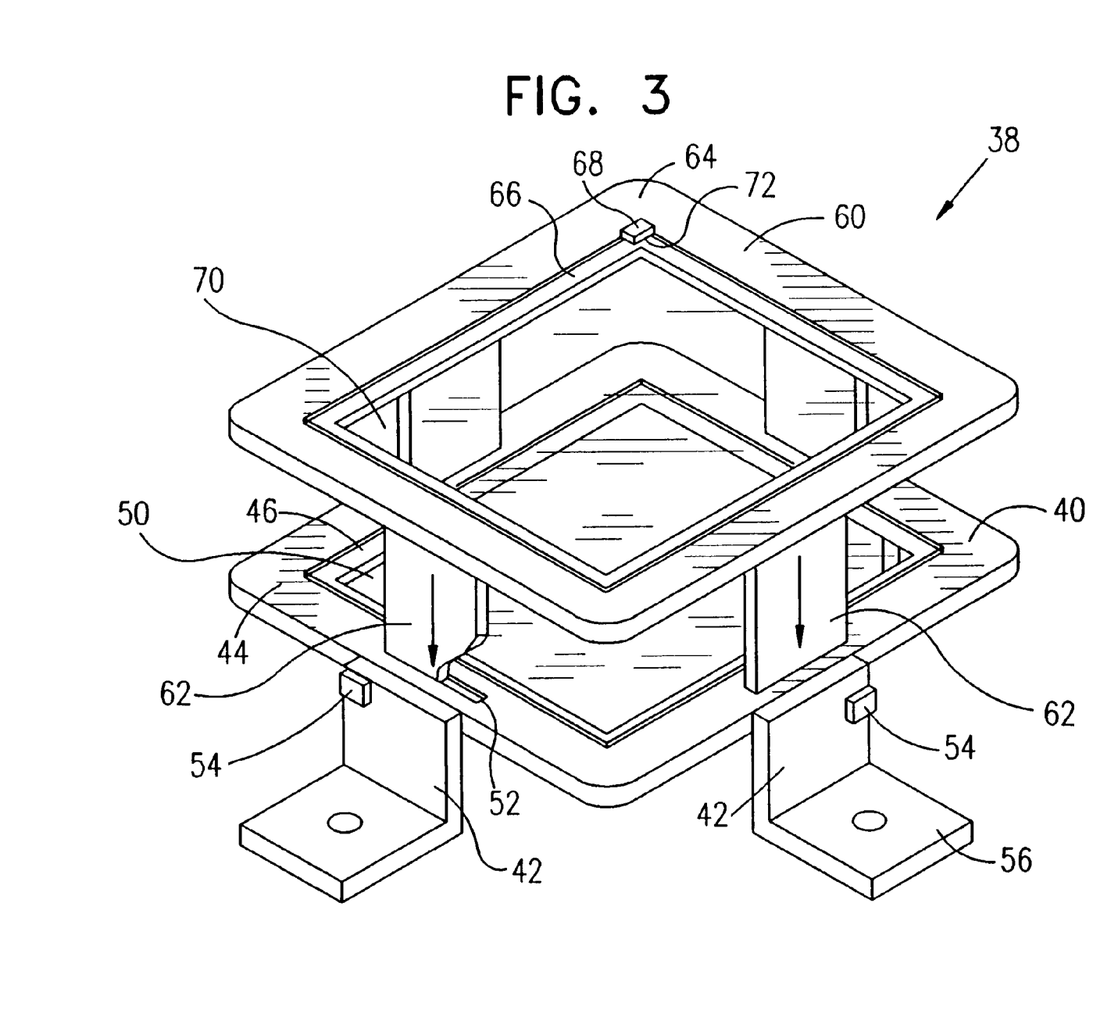
FIG. 3 is an enlarged perspective view of the frame set of one embodiment of the invention.

Reference is now made to FIG. 3, which shows frame set 38 in detail. In one preferred embodiment of the present invention, frames 40 and 60 are preferably rectangular, with their outer corners preferably rounded to avoid injury to patient 20 or to the surgeon from sharp corners. The sizes of frames 40 and 60 are preferably the same, and are chosen to be large enough to allow a large field for the biopsy procedure. The sizes of frames 40 and 60 are generally limited by the area in patient's body 20 to which frame-set 38 is to be connected, since frame 40 must be connected firmly to patient's body 20. Alternatively, in some cases, a small frame set 38 may be used to simplify the procedure. In another preferred embodiment frame 60 is larger than frame 40, allowing more freedom of movement for the surgeon.

Frames 40 and 60 are constructed of a rigid material, so that frames-set 38 does not change its configuration unintentionally. However, frame-set 38 is preferably slightly elastic, allowing the surgeon to distort frame-set 38 by small amounts in case small changes in trajectory 80 are necessary during the biopsy procedure. Preferably, such changes are verified using one of the verification methods described herein. It should be appreciated, that as needle 36 advances into the body, variations in trajectory 80 are increasably difficult. The material of frames 40 and 60 preferably does not interact with imaging system 24 (i.e., it is transparent to x-rays in a CT device), thus allowing markers 54 to be imaged with a high contrast. When using CT devices for imaging frames 40 and 60 are preferably comprised of plastic such as Lexan or polyethylene having low radiation absorption. Markers 54 are accordingly comprised of a highly absorbing material such as lead or aluminum.

Frames 40 and 60 preferably comprise an outer thick frame 44 (64), an inner thinner ledge 46 (66) and a rectangular opening. Outer frames 44 (64) and inner ledges 46 (66) are preferably coplanar on their bottom surface, which faces the patient, while on top, ledges 46 (66) form an indented area in which sheets 50 (70) are accurately placed.

Sheets 50 and 70 are comprised of a material which can be easily perforated and can be marked. Alternatively, the marks are printed on a suitable material which is overlaid or glued to the sheets. Preferably, sheets 50 and 70 are made of aluminum and are about 250 micrometers thick. At that thickness, aluminum is substantially transparent to x-ray radiation. Alternatively, sheets 50 and 70 are made of a transparent material allowing the surgeon to see patient's body 20 beneath sheets 50 and 70.

Frame 40 preferably has four legs 42 to enable easy connection to patient's body 20. Preferably, legs 42 have flat bases 56, preferably, formed from flat pieces shaped to enable strong and precise connection of frame-set 38 to patient 20. Preferably, frame 60 has four legs 62 which connect upper frame 60 to lower frame 40. Legs 62 separate lower frame 40 from upper frame 60 and therefore their height determines the accuracy of the insertion angle. The height of legs 62 is therefore, preferably, larger than the height of legs 42. Within lower frame 40 there are, preferably, four receptacles 52 which are formed to precisely receive legs 62. These receptacles allow precise connection of frame 40 to frame 60. Preferably, fiducial markers 54 are embedded within legs 42 (62) at clearly observable locations.

Information to assist positioning of sheets 50 (70) within frames 40 (60) is, preferably, printed on the sheets. The information includes identifying the sheet as upper sheet 70 or lower sheet 50, defining the sheet's orientation, i.e., which corner is the top right corner and specifying which surface of the sheet faces the patient. The surface of sheets 50 and 70 which faces the patient, is preferably colored with a different color than the upper surface of the sheets. Preferably, in addition, on both sheets 50 and 70 the words lower and upper, respectively, are clearly printed. The orientation of the surface within the frame can be designated by a mark in the top right corner, or by any other clear indication.

Preferably, one of the corners of frame 60 has a key 68 and the corresponding corner of sheet 70 has an indent 72 which allows positioning of the sheet only in the correct orientation. Preferably, a similar technique is used for sheet 50. In addition, preferably, there is a slight difference in size between lower sheet 50 and upper sheet 70 to assure that the sheets are placed in the correct frame.

In order to insert lower sheet 50 into its frame 40, upper frame 60 is lifted from frame 40 and returned to place after sheet 50 is placed. Receptacles 52 allow for the accurate replacement of upper frame 60.

Figure 4A:
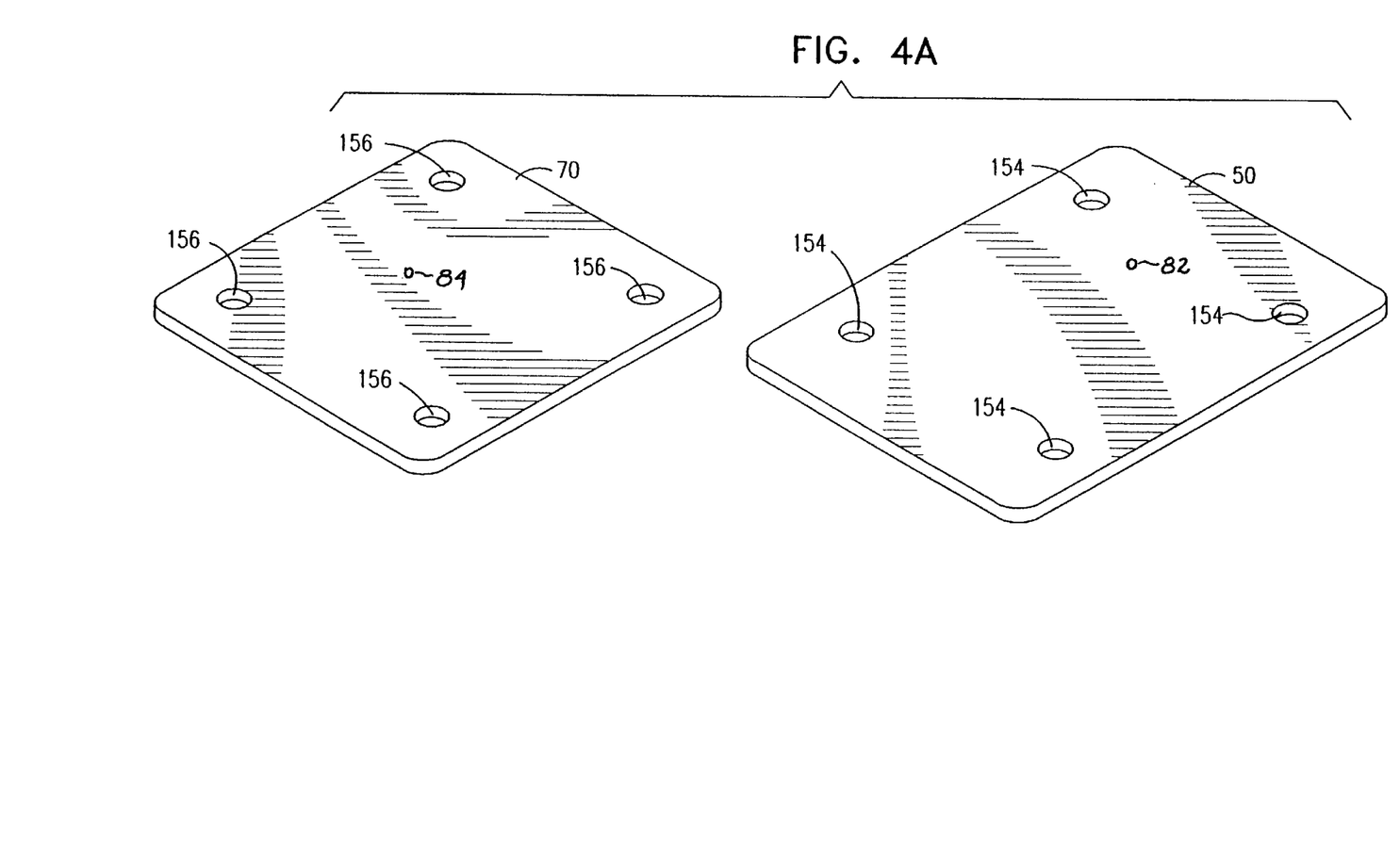
FIG. 4a and 4b are enlarged perspective views of a frame set of another embodiment of the invention.
Figure 4B:
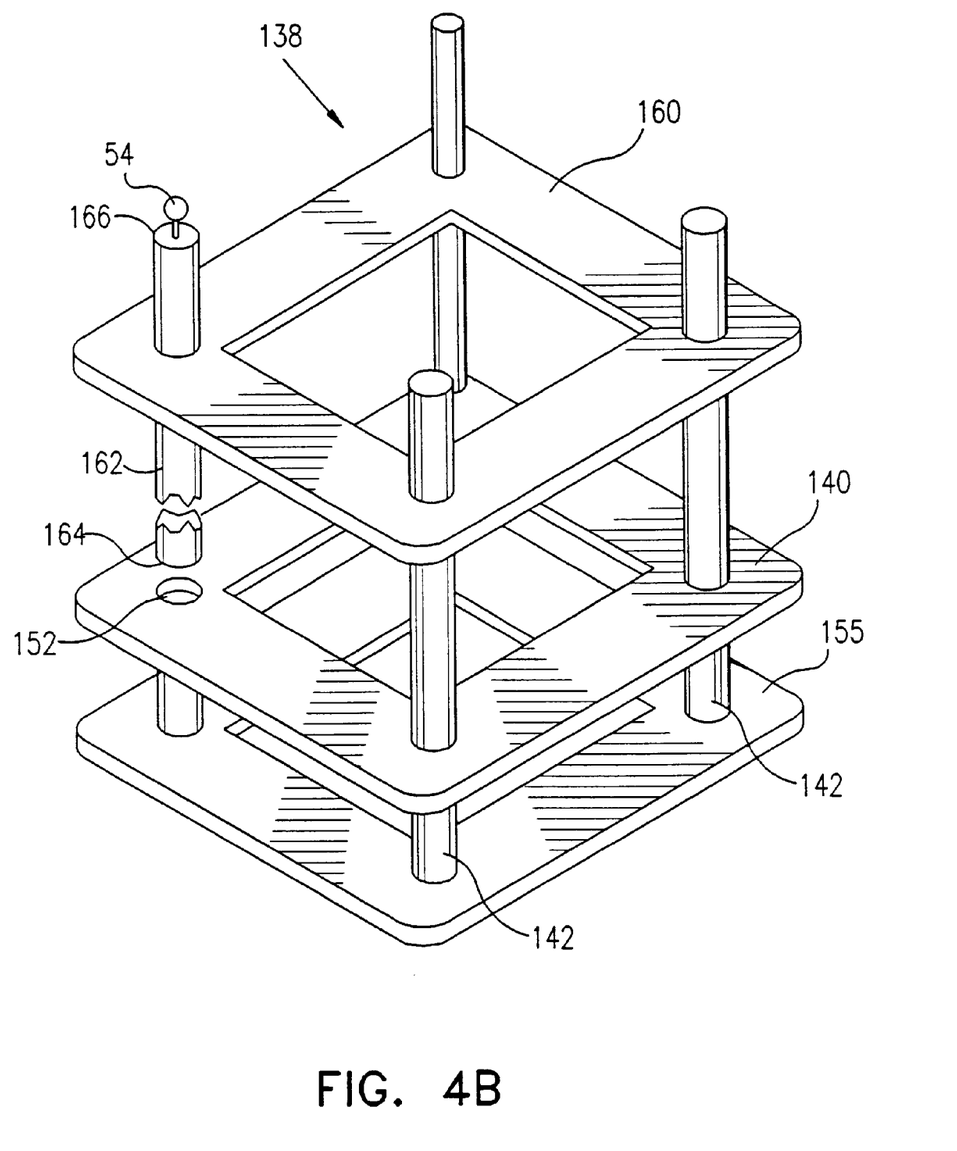

Reference is now made to FIG. 4B which shows a frame set 138 in accordance with another preferred embodiment of the invention. Frame set 138 includes a base-frame 155 for easy attachment to the body, an upper frame 140 and a lower frame 160. Frames 140 and 160 are preferably rectangular, preferably, with their outer corners rounded. The size of frames 140 and 160 is preferably the same.

Frame 140 preferably has a leg 142 at each corner of the frame. Legs 142 are preferably connected to base frame 155 which may be easily connected to patient 20. Within lower frame 140, on its top surface, there are, preferably, receptacles 152. Preferably, extending through frame 160 there are legs 162, located at each corner of frame 160. Preferably, each leg 162 has on one end a tip 164 which is precisely received by receptacles 152, and on the other end 166 there is a marker 54.

Reference is now made to FIG. 4A, which shows sheets for placement within frame set 138. As shown in FIG. 4A, in this embodiment holes 154 and 156, intended to receive legs 162, are perforated in sheets 50 and 70, respectively. Holes 154 and 156 are preferably, automatically perforated by a computer controlled device (not shown). Referring back to FIG. 4B, in order to place sheet 50, frame 160 is lifted and holes 154 are aligned with receptacles 152. Legs 162 are returned to receptacles 152 through holes 154 which tightly receive legs 162. Sheet 70 is now placed on frame 160, holes 156 tightly receiving upper parts of legs 162. Preferably, at least one of legs 162 is of a different thickness than the others, so that sheets 50 and 70 can be situated only in their proper positioning. In addition, preferably, one of legs 162 has a different thickness at its lower and upper parts to prevent interchanging between sheets 50 and 70.

This embodiment allows sheets 50 and 70 to be larger than frames 140 and 160 and therefore allows the surgeon more maneuverability. In particular, sheet 70 may be larger than sheet 50 allowing large angles between trajectory 80 and an axis perpendicular to the patient.

Holes 82 and 84 are produced in a similar manner to that disclosed above with respect to FIGS. 2 and 3. All other details of this embodiment are as described above with respect to FIG. 3.

Figure 5:
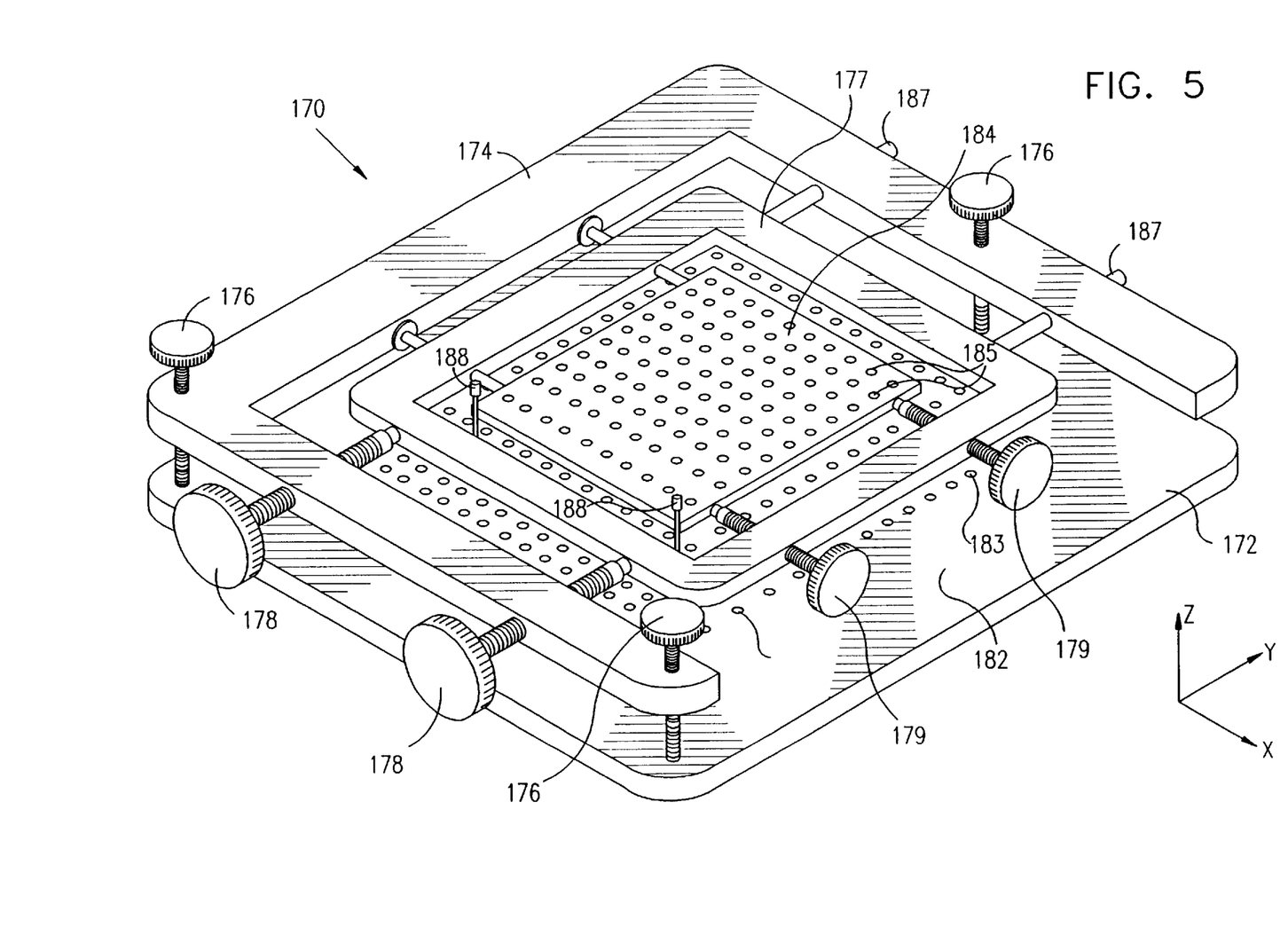
FIG. 5 is an enlarged perspective view of the frame set of yet another embodiment of the invention.

Reference is now made to FIG. 5, which shows a frame set in accordance with another embodiment of the present invention. Frame set 170 is comprised of an upper slideable frame 174 and a lower stationary frame 172. Lower frame 172 is preferably constructed similarly to either of frames 40 or 140 and is likewise fastened to patient 20. A sheet 182 containing an array of holes 183 is, preferably, permanently situated in frame 172, preferably, integral with frame 172. Upper frame 174 is situated above frame 172, either fixedly, with a plurality of supports or with a plurality of screws 176, preferably three, adjustably setting the distance between frames 174 and 172. An inner frame 177 is movably connected by at least one screw 178 to frame 174. At least two guides 187 are connected to frame 177 and run through frame 174, thus supporting frame 177 on the opposite side of frame 177 from screw 178. A second screw 178 may be provided, whereby when one of screws 178 is turned and frame 177 is moved, the other screw turns passively. Another set of screws 179 runs through a second sheet 184 and connects it to inner frame 177 in a similar manner. Thus, the position of sheet 184 can be adjusted in both x and y directions, by turning screws 178 and 179. Preferably, screws 178 and 179 come with an accurate measuring system such as micrometers, allowing the surgeon to easily perform exact movements of the sheets.

Sheet 184 contains an array of holes 185, similar to array of holes 183. Holes 183 and 185 are uniquely indicated, preferably numbered, so that computer 26 can clearly relate to the surgeon a specific hole. After the surgeon marks trajectory 80 on an image, computer 26 indicates to the surgeon through which holes biopsy needle 36 should be guided and any adjustments required (if necessary) in the height and lateral position of sheet 184. In a preferred embodiment of the invention the movements of sheet 184 are performed automatically by computer controlled micrometers. Once frame 184 is properly located, it is preferably fixed to lower frame 172 by screws 188 or by any other method of preventing undesired movements. If an error in the biopsy needle position is detected during the biopsy procedure, screws 188 may be released and the position of frame 174 changed. It is noted that in further embodiments sheet 182 may also be movable, in a similar fashion as sheet 184, allowing for even more freedom in planning trajectory 80 and in attaching the frame-set to the body.

Figure 6:
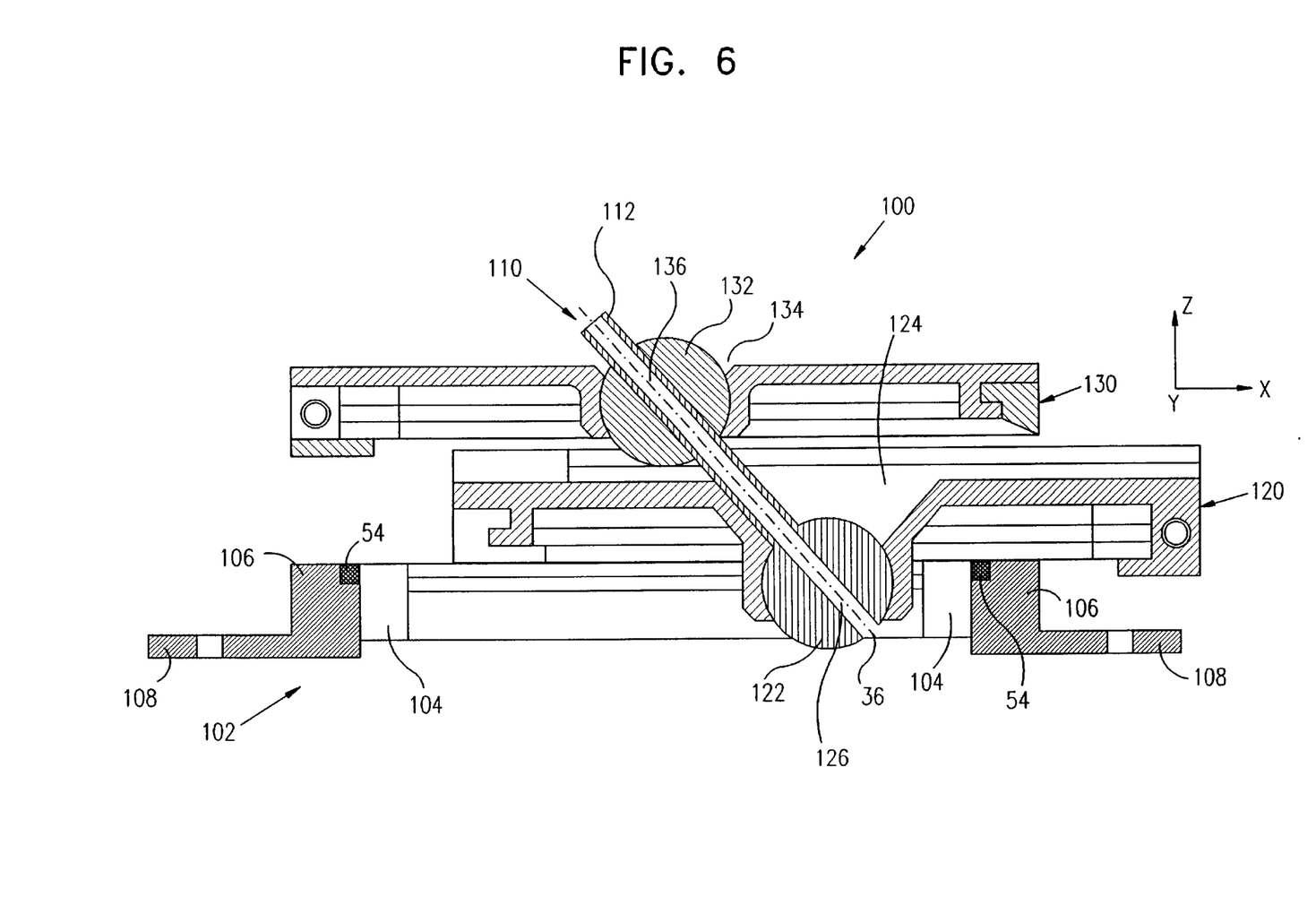
FIG. 6 is a cross sectional view of a plane set used in yet another embodiment of the present invention.

In some embodiments of the present invention instead of frame-sets 38 or 138, the biopsy needle is inserted through a guide embedded within an alternative plane-set. Reference is made to FIG. 6, which illustrates a plane set 100 with a guide in accordance with a preferred embodiment of the present invention. Plane-set 100 is comprised of a base frame 102, two movable planes 120 and 130 and a guide 110 embedded within the planes. Guide 110 is comprised of an elongate tube 112, and two spherical portions 122 and 132. Guide 110 supports a biopsy needle during scanning, and accurately guides the needle along trajectory 80. Elongate tube 112, is a long tube open on both ends, with an inner diameter which tightly receives the biopsy needle. Elongate tube 112 is firmly situated in a hole 126 running through spherical portion 122; preferably, tube 112 is integral with spherical portion 122. Tube 112 is also tightly situated within a hole 136, running through the center of spherical portion 132. However, tube 112 is preferably free to slide within hole 136. Tube 112 may have a removable inner wall which fills in the space between tube 112 and the needle. Inner walls of different thickness can allow use of needles of different diameters.

Planes 120 and 130 are preferably rectangular rigid solid members, with outer rounded corners. Within planes 120 and 130, preferably in their centers, holes 124 and 134 are formed, respectively, in which spherical portions 122 and 132 respectively, are held. Spherical portions 122 and 132 have outer smooth surfaces so that holes 124 and 134 hold portions 122 and 132 in place and allow them to rotate. The walls of hole 124 preferably extend beneath plane 120, and are, preferably, an integral part of plane 120. The lower part of hole 124 is formed to tightly receive spherical portion 122. The upper part of hole 124 has the shape of a cone, widening upward, allowing guide 110 to move without interference. The upper inner walls of hole 124 serve as stoppers which prohibit movement of guide 110 beyond allowed angles. Hole 134 which extends through plane 130 is preferably substantially spherical.

Frame 102 serves as a stand on which plane 120 can slide, and in which guide 110 can move without touching patient 20. One side of base frame 102 is connected to patient 20, and the other side of frame 102 supports plane 120. Frame 102 is comprised of an outer frame 106, which is, preferably, rectangular with rounded outer corners, and preferably an inner soft stopper 104, which softens any possible collision between the lower walls of hole 124 and frame 102. On the side to be connected to patient 20, frame 102 preferably has a ledge 108 which facilitates its connection to patient 20. The connection is performed in any of the methods mentioned above with regard to frame set 38.

Fiducial markers 54 are preferably embedded within frame 102, the stationary part of plane set 100. Plane set 100 is preferably comprised of materials as described above regarding frame set 38 to provide good imaging contrast for markers 54.

Both planes 120 and 130 slide independently of each other in both transverse (x and y) directions, preferably, with accurate measurement of their movements. Each of planes 120 and 130 preferably has at least one micrometer which controls its movements, and also provides an indication of its position.

After plane-set 100 is fastened to patient 20, the CT imaging system preferably performs a volumetric scan, such as a helical scan, of a region containing lesion 32. Consequently, computer 26 and the surgeon perform actions as described above regarding frame-set 38. After computer 26 calculates the coordinates of trajectory 80, as described above, computer 26 gives the surgeon instructions to slide planes 120 and 130 into a position such that guide 112 is collinear with trajectory 80. A preferred embodiment of the software which performs these calculations is attached in software appendix A. Alternatively, using computer controlled micrometers, the necessary movements are performed automatically.

It is noted that if only one of planes 120 and 130 is moved, spherical portions 122 and 132 rotate and guide 110 changes its angle relative to frame 102. However, if both planes 120 and 130 slide in the same direction for the same distance only the position of guide 110 changes and the angle remains unchanged.

A laser beam, which illuminates the extra-body portion of trajectory 80 may also be used for verification of the path of the needle.

A tracking device can be used in conjunction with any of the above mentioned embodiments of the invention to improve the accuracy of the biopsy procedure. The tracking device is attached to the biopsy needle, so that the position and orientation in space of the needle can be determined at any moment. The tracking device can be any of those known in the art. Preferably, three of markers 54 embedded within one of the frame sets are selected to define a reference frame which defines a coordinate system. Preferably, the three markers 54 are located on the same frame (either frame 40 or frame 60). It should be noted that although markers 54 have been mentioned, any three non-collinear points, fixed relative to the patient, can be used to form the coordinate system. The selection is usually performed by the surgeon by indicating the three chosen points on one of the images. Alternatively, when markers 54 are used, the computer can choose the three points by automatically finding three of markers 54 according to their shape and their computed density.

Responsive to a determined position of the biopsy needle, computer 26 may display image slices of the patient. Such images may be prepared ahead of time. Alternatively, images are created from raw data only when required.

Before inserting the biopsy needle into the patient, the needle is brought to an initialization point, which is preferably clearly marked on one of the frames. Preferably, all through the biopsy procedure, computer 26 continuously keeps track of the position and orientation of the biopsy needle, with respect to the predefined coordinate system.

The surgeon may instruct control unit 30 orders to have screen 28 constantly show images of slices containing the distal end of the biopsy needle. Computer 26 selects an image containing the tip of the needle for display, responsive to the determined location of the needle. The display is updated at a suitable rate, such as about three images a second. Thus the surgeon has a real time picture of the needle's trajectory, without continuously exposing the patient to radiation from imaging system 24.

Since the biopsy needle is held within guide 110 (FIG. 6) or within a frame set such as described in any of the above embodiments, scanning of patient 20 by imaging system 24 may be performed without removing the biopsy needle. Such scanning may be desired just before inserting the biopsy needle, and/or at any time during the invasive procedure. The surgeon may initiate a verification scan to insure that neither patient 20 nor his inner organs have moved substantially since the previous scan. A scan may also be made in order to check that the needle is following the trajectory 80 (FIG. 2). Such verification scans are performed, for example, before important steps such as taking tissue samples during a biopsy.

The surgeon may instruct computer 26 to cause imaging system 24 to perform an axial scan of a required slice. Such slice would be, for example, one containing the tip of needle 36 and destination point 88. Alternatively the scan the scan may produce a slice following the trajectory of needle 36. The bed consequently is properly set either manually, according to instructions produced by computer 26, or automatically. The imaging system then performs an oblique scan using any of the methods available for such scans, and produces a new image.

The new image may be used instead of or in addition to the original image which appears on screen 28. The insertion process proceeds with the new image, and if necessary corrections may be made in trajectory 80 or a new trajectory is chosen for needle 36.

Alternatively, screen 28 displays two images, the new image produced in the most recent scanning and a corresponding image of the same slice from the original scan, showing the slice as it was when trajectory 80 was planned. By comparing the trajectory of biopsy needle 36 in both images the surgeon can determine if needle 36 is following the proper trajectory.

Figure 7:
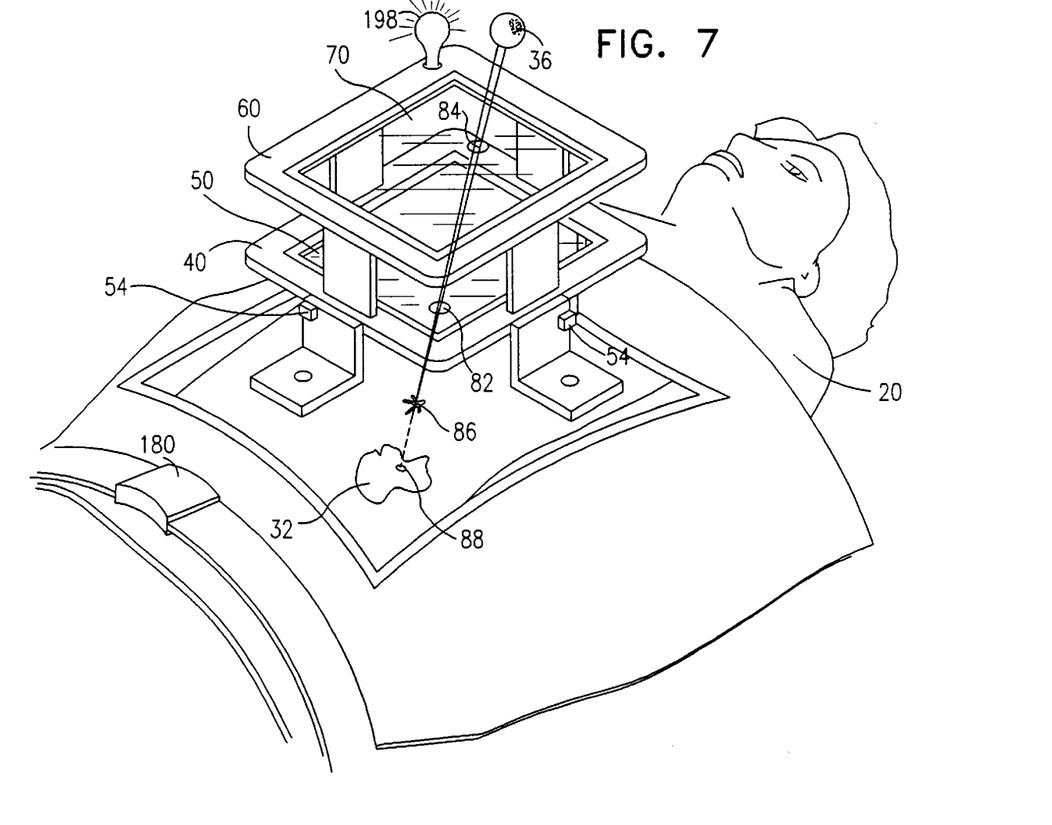
FIG. 7 is a perspective view of a patient illustrating the use of a frame set and a respiratory belt in accordance with a preferred embodiment of the invention.

In some embodiments of the present invention a respiratory belt is used to additionally enhance accuracy of the procedure. Referring to FIG. 7, which illustrates the use of a respiratory belt, a patient 20 has a frame-set or plane set, connected to his body. Surrounding patient 20, in the area of his abdomen or thorax, is a respiratory belt 180 which measures the movement and/or pressure changes related to respiratory activity. Alternatively, impedance measurements may be used to monitor the respiratory cycle. The measurements from respiratory belt 180 are passed to computer 26. Computer 26 will gate all automatic stages such as imaging to be performed at the same portion of the respiratory cycle. In addition a signaling device, such as a light 198 or a bell may be used to notify the surgeon of a particular phase of the respiratory cycle (such as when there is little motion). Light 198 is preferably situated in a convenient place for the surgeon to see it, such as on belt 180 or on frame-set 38. Preferably, before the biopsy procedure, computer 26 finds a portion of the respiratory cycle of patient 20 in which there is little movement and signals for all actions to be performed in that portion.

It will be appreciated that the preferred embodiments described above are cited by way of example, and the full scope of the invention is limited only by the claims.

What is claimed is:

1. A method for positioning an invasive tool which comprises:

attaching a frame to a human body adjacent to a portion of the body;

acquiring an image of the body portion, referenced to the frame;

determining a trajectory of the tool on the image;

calculating points of intersection between the trajectory and two sheets which are adapted to be inserted in the frame;

perforating the sheets at the calculated points, at least one of said perforations being made responsive to the calculation;

placing the perforated sheets within the frames; and inserting the invasive tool through the perforations, so that it is positioned for insertion into the body portion.

2. A method as in claim 1 wherein acquiring an image and insertion of the invasive tool are performed in substantially the same stage of the respiratory cycle.

3. A method for positioning an invasive tool which comprises:

attaching a frame with two apertured sheets to a human body;

acquiring an image of the body portion, referenced to the frame;

determining a trajectory of the tool on the image;

calculating points of intersection between trajectory and the two sheets;

moving the sheets so that two apertures, one of which is on each of the sheets, define the trajectory; and inserting the invasive tool through the apertures, so that it is positioned for insertion into the body portion.

4. A method as in claim 3 wherein acquiring an image and insertion of the invasive tool are performed in substantially the same stage of the respiratory cycle.

5. Apparatus for leading a biopsy needle into a portion of the human body comprising:

a first apertured substantially rigid sheet;

a second apertured substantially rigid sheet, having a generally fixed relationship with the first sheet; and a frame, connectable to the body, on which the first and second sheets are mountable and which provides a suitably constant position for the first and second sheets relative to and on the same side of the body portion.

6. Apparatus as described in claim 5 wherein the frame comprises a lower frame and an upper frame removably connected to the lower frame.

7. Apparatus according to claim 6 wherein the frame comprises fiduciary marks.

8. Apparatus according to claim 6 wherein the sheets are comprised of a transparent material.

9. Apparatus as described in claim 5 wherein the frame comprises fiduciary marks.

10. Apparatus according to claim 9 wherein the sheets are comprised of a transparent material.

11. Apparatus as described in any of claims 5, wherein the sheets are comprised of a transparent material.

12. Apparatus for leading an invasive tool into a human body comprising:

a first substantially rigid sheet;

a second substantially rigid sheet, precisely movable with respect to the first sheet; and a frame connectable to the body which provides a suitably constant position for the first and second sheets relative to and on the same side of said body portion, wherein, each of the sheets defines a hole therethrough, wherein the holes are adapted to receive the invasive tool.

13. Apparatus in accordance with claim 12, wherein at least one of the sheets defines a plurality of holes therethrough.

14. Apparatus according to claim 8 wherein said precise relative motion is at least in a direction parallel to its surface.

15. Apparatus as described in claim 14, comprising a guide for the invasive tool inserted in the holes.

16. Apparatus according to claim 15 comprising a micrometer for moving the second sheet relative to the first sheet.

17. Apparatus according to claim 15 wherein the first sheet is precisely movable with respect to the frame.

18. Apparatus according to claim 15 wherein at least one of the sheets defines a plurality of holes therethrough.

19. Apparatus in accordance with claim 14, comprising a micrometer for moving the second sheet relative to the first one.

20. Apparatus according to claim 19 wherein the first sheet is precisely movable with respect to the frame.

21. Apparatus according to claim 19 wherein at least one of the sheets defines a plurality of holes therethrough.

22. Apparatus in accordance with claim 14, wherein said micrometer is computer controlled.

23. Apparatus according to claim 22 wherein the first sheet is precisely movable with respect to the frame.

24. Apparatus according to claim 22 wherein at least one of the sheets defines a plurality of holes therethrough.

25. Apparatus in accordance with claim 14, wherein the first sheet is precisely movable with respect to the frame.

26. Apparatus according to claim 25 wherein at least one of the sheets defines a plurality of holes therethrough.

27. Apparatus in accordance with claim 14, wherein the frame comprises fiduciary marks.

28. Apparatus according to claim 27 wherein at least one of the sheets defines a plurality of holes therethrough.

* * * * *